United States Patent [19]

Deschler et al.

[11] Patent Number: 4,697,009

[45] Date of Patent: Sep. 29, 1987

[54] N-SILYLPROPYL-N'-ACYL-UREAS AND PROCESS FOR THEIR PRODUCTION

[75] Inventors: Ulrich Deschler; Peter Kleinschmit, both of Hanau; Rudolf Michel, Freigericht, all of Fed. Rep. of Germany

[73] Assignee: Degussa Aktiengesellschaft, Frankfurt am Main, Fed. Rep. of Germany

[21] Appl. No.: 875,867

[22] Filed: Jun. 18, 1986

[30] Foreign Application Priority Data

Jul. 6, 1985 [DE] Fed. Rep. of Germany ....... 3524215

[51] Int. Cl.$^4$ ................................................ C07F 7/10
[52] U.S. Cl. ..................................... 540/487; 556/414; 556/421; 544/229; 546/14; 548/110

[58] Field of Search ....................... 556/421; 544/229; 546/14; 548/110; 260/239 BC; 556/414; 540/487

[56] References Cited

U.S. PATENT DOCUMENTS

| | | | |
|---|---|---|---|
| 2,857,430 | 10/1958 | Applegath et al. | 556/421 X |
| 2,907,782 | 10/1959 | Pike | 556/421 |
| 3,793,253 | 2/1974 | Quiring et al. | 556/421 X |
| 3,803,194 | 4/1974 | Golitz et al. | 556/421 X |
| 3,856,756 | 12/1974 | Wagner et al. | 556/421 X |

Primary Examiner—Paul F. Shaver
Attorney, Agent, or Firm—Cushman, Darby & Cushman

[57] ABSTRACT

The invention is directed to N-silylpropyl-N'-acyl ureas and their production from an alkali cyanate, a 3-halopropylsilane and in a given case, a cyclic acidamide. By heating the compounds of the invention the blocked isocyanate function can be set free.

16 Claims, 3 Drawing Figures

Fig. 2. ¹H-NMR-SPECTRUM (250MHz) OF SL 30-3-1

IR-SPECTRUM OF 30-3-1

N-SILYLPROPYL-N'-ACYL-UREAS AND PROCESS FOR THEIR PRODUCTION

BACKGROUND OF THE INVENTION

The invention is directed to N-silylpropyl-N'-acyl-ureas, a process of their production and the setting free of the blocked isocyanate function.

Silanes of the general structure I have large scale significance as coupling agents in material systems which consist of an inorganic and an organic phase, as well as for the modification of OH functional surfaces:

$$(R^4O)_3Si-CH_2-CH_2-CH_2-X \quad (I)$$

$(R^4=CH_3, C_2H_5)$

The most important functional groups include: $X=NH_2$, $-S_4-$ (Si 69), $-SH$, $-Cl$, $-O-CO-C(CH_3)=CH_2$ and $$-O-CH_2-CH\underset{O}{\overset{}{\diagdown\diagup}}CH_2$$

The isocyanate function ($X=-NCO$) represents a particularly valuable functional group:

On the one hand it can be reacted with numerous H-acidic, monomeric materials (amines, alcohols, oximes, and many others) with the formation of newer functional silanes, on the other hand it can also react with polymeric resins and rubbers in mutual binding. In contrast to the advantage of the multifold chemical activity there is the disadvantage of the high toxicity of the isocyanate group and the cumbersome synthesis of the silane (II) in practice (Hedaya U.S. Pat. No. 4,130,576):

$$(R^4O)_3Si-C_3H_6-NCO \quad (II)$$

In industry therefore there are frequently employed blocked alkyl and aryl isocyanates: (Z. W. Wicks, Progr. Org. Coat. Volume 9, (1981) pages 3-28.

As blocking agents for the non-silyl containing organic isocyanates there are used, e.g. alcohols (especially phenols), β-dicarbonyl compounds, lactams or oximes. Blocked isocyanates on the one hand are usable from aqueous systems and on the other hand relatively inexpensive procedures are sufficient for safely handling them because of their comparatively low toxicity.

In Berger U.S. Pat. No. 3,994,951 there is described a hydrolyzable silane from which the isocyanate function is set free at a temperature of 160° C. which silane is O-methyl-N-trimethoxysilyl-propyl-urethane.

This compound, however, is little suited for use as an coupling agent in filler reinforced polymer systems for the reason that the thermolysis only proceeds at relatively high temperatures and the byproduct methanol (flash point: 11° C.) formed makes it necessary to take corresponding safety precautions.

The thermolysis of O-methyl-N-trimethoxysilylpropyl urethane can only be carried out in good yields if there is used very slow thermolysis. The cause of this must be that the thermolysis byproduct methanol is more volatile than the desired 3-isocyanatopropyltrimethoxysilane, so that in the distillative separation of the latter silane from the thermolysis sump the recombination of methanol and 3-isocyantopropyltrimethoxysilane in the gas phase can only be prevented if this separation is carried out comparatively slowly. The thus attainable time-space yields are unsatisfactory for an industrial process.

The same is true for the process for the production of 3-isocyanatopropylsilanes by gas phase esterification of 3-isocyanatopropyltrichlorosilane with alcohols (Bennett U.S. Pat. No. 3,651,117) in which the simultaneously undesired side reaction of the isocyanate group with the alcohol can be suppressed only through an industrially expensive procedure.

The invention is directed to hydrolyzable silanes having a blocked isocyanate function and a process for their direct production in high yields.

Simultaneously the isocyanate group should quite easily be set free by thermolysis.

SUMMARY OF THE INVENTION

The present invention is directed to N-silylpropyl-N'-acyl-ureas of the formula:

$$\underset{\underset{A-C-NH-C_3H_6-Si(CH_3)_x(OR)_{3-x}}{\overset{O}{\|}}}{} \quad (III)$$

in which
x is 0, 1, or 2
R is $C_1$-$C_6$ alkyl, straight chain or branched, (2'-methoxy)ethyl, aryl, preferably phenyl
A is $$\underset{\underset{-N-C-R^2}{\overset{R^1 \quad O}{| \quad \|}}}{}$$

where $R^1$ is $C_1$-$C_6$ alkyl, straight chain or branched, $R^2$ is hydrogen, $C_1$-$C_6$ alkyl, straight chain or branched, or
A is $$-N\diagdown\diagup\underset{CO-(CH_2)_y}{\overset{CH_2-D}{}}$$

where y is 1, 2, or 3 and D is $-CH_2-$, $>NR^1$.

These compounds for example, can be applied to glass fibers from aqueous solution, which fibers are designed to be worked into synthetic resins. After thermal and/or catalytic treatment the cross-linking can be carried out via the then set free isocyanate.

A further subject matter of the invention is a process for the production of compounds of formula (III) by mixing in an aprotic, polar organic solvent equimolar amounts of an alkali cyanate (e.g. sodium cyanate or potassium cyanate), a 3-halopropyl silane of the formula:

$$X-C_3H_6-Si(CH_3)_x(OR)_{3-x} \quad (IV)$$

and a compound of the formula:

$$\underset{R^2-C-NH-R^1}{\overset{O}{\|}} \text{ or} \quad (V)$$

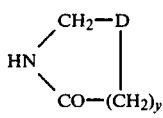
(VI)

preferably in this sequence, wherein R, R¹, R², D, x, and y are as defined above and X is Cl, Br, or I, subsequently reacting them with each other at elevated temperature, after the end of the reaction and cooling the reaction mixture to room temperature filtering off the precipitated alkali halide and distilling off the solvent from the filtrate.

The desired product remains behind and can be used without further purification.

The reactants can be quickly mixed together at room temperature, without fear of starting a reaction.

The reaction is carried out at a temperature of 100°–140° C. within 1–8 hours, preferably 100°–130° C. within 4 hours under a protective gas atmosphere. As protective gases there are especially suitable nitrogen and argon.

In using the preferably employed cyclic amides the reaction proceeds according to the following scheme:

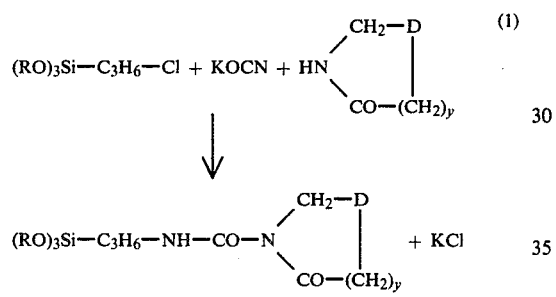

As solvents there are suitable N,N-dimethylformamide, N,N-dimethylacetamide, N,N,N',N'-tetramethylurea, N,N,N',N'-tetramethylenediamine, N-methylpyrrolidone, dimethylsulfoxide, hexamethylphosphoric acid triamide. Especially preferred is N,N-dimethylformamide.

Per mole of silane employed there is used 250–400 ml of solvent, preferably 300 ml.

As alkali cyanates there can be used sodium cyanate and especially potassium cyanate.

Suitable silanes are: 3-chloropropyltrimethoxysilane, 3-chloropropyltriethoxysilane, 3-chloropropyltri-i-propoxysilane, 3-chloropropyltri-n-propoxysilane, 3-chloropropyltri-t-butoxysilane, 3-chloropropyltri(2'-methoxy)ethoxysilane, 3-chloropropyldimethoxymethylsilane, 3-chloropropyldiethoxymethylsilane, 3-chloropropylmethoxydimethylsilane, 3-chloropropylethoxydimethylsilane, 3-chloropropyltriphenoxysilane and the corresponding Br- and I-substituted analogous compounds, e.g. 3-bromo-propyltriethoxysilane and 3-iodopropyltri-i-propoxysilane.

Of these compounds there are preferably employed: 3-chloropropyltrimethoxysilane, 3-chloropropyldimethoxymethylsilane, 3-chloropropyltriethoxysilane, and 3-chloropropyldiethoxymethylsilane.

As amides there are employed: N-methylformamide which is preferred and N-methylacetamide, and the corresponding ethyl-, propyl, and phenyl-substituted amides, N-methylpropionamide, N-methylvalerylamide, and N-methylbutyramide and the corresponding ethyl and phenyl-substituted amides; N-methylphenylacetamide, N-methylcapronic acid amide, N-methyllaurylamide, N-methyloleylamide, N-methylpalmitylamide, N-methylstearylamide, N-methylbenzamide, N-methyltolylamide, cyclic:

2-pyrrolidone, 1-N-methyl-hexahydro-1,4-diazepinone of the formula

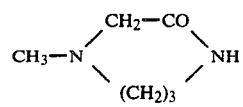

2-piperidone and especially ε-caprolactam.

The desired N-acyl ureas are obtained according to the process of the invention in high yield.

Members of this new class of compounds are yellow oils as crude products.

They can be decomposed thermally at temperatures of ≧135° C. for example according to the following equation (2) in which case the decomposition temperature can be lowered still further through the addition of catalytic amounts of dibutyltin dilaurate.

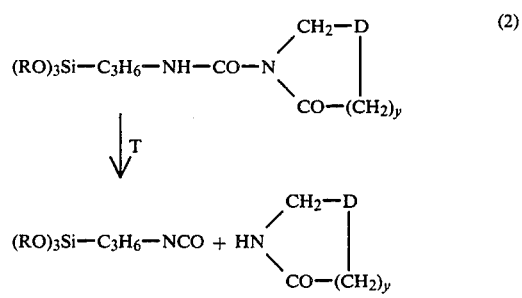

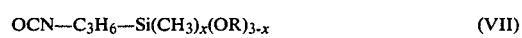

There are formed 3-isocyantopropylsilanes of the formula $$OCN-C_3H_6-Si(CH_3)_x(OR)_{3-x} \qquad (VII)$$

The thermolysis of the compounds of the invention preferably takes place in a vacuum distillation apparatus at pressures of 100 to 6500 Pa, preferably of 200 to 2000 Pa and a sump temperature between 130° and 160° C.

Thereby it has been found favorable that, in contrast to the process according to Berger U.S. Pat. No. 3,494,951, the boiling point of the blocking agent as a rule is above that of the isocyanatopropylsilane, so that there does not occur a recombination of the materials in the gas phase above the distillation sump.

The thermolysis temperature can be lowered through addition of catalytic amounts of dibutyltin dilaurate, especially 0.5 to 5 mole% based on the acylurea, so that thermolysis can be carried out at a temperature of 115° C.

The process can comprise, consist essentially of, or consist of the stated steps with the recited materials.

Unless otherwise indicated all parts and percentages are by weight.

DETAILED DESCRIPTION

All reactions were carried out in standard laboratory apparatus under a protective gas atmosphere, (e.g. nitrogen) as follows:

Equimolar amounts of potassium cyanate, 3-chloropropylalkoxysilane and carboxylic acid amide were mixed in this sequence in dimethylformamide (300 ml/mole alkali cyanate) and heated to about 110° C. with stirring within 30 minutes. A slight exotherm was observed at this temperature, through which the temperature spontaneously rose up to about 130° C. Stirring was continued for a further 4 hours at 130° C. After cooling the reaction mixture it was filtered off from precipitated alkali chloride and the solvent drawn off. The title compounds then remained as yellow, viscous liquids, which did not need any further purification step prior to use.

EXAMPLE 1

There were added at room temperature under protective gas (nitrogen) the following materials in the listed sequence within 5 minutes to a 4 liter three neck flask equipped with a KPG stirrer and water condenser.

900 ml DMF
235.5 g≅3.0 mole potassium cyanate
722.4 g≅3.0 mole 3-chloropropyltriethoxysilane
339.5 g≅3.0 mole ε-caprolactam The reaction mixture was then heated to about 110° C. within 30 minutes. A slight exotherm occurred at this temperature. The temperature of the reaction was not allowed to exceed 130° C. and the reaction proceeded for a total of 4 hours at 130° C. After cooling the reaction mixture the precipitated potassium chloride was filtered off, the precipitate washed three times, each time with 100 ml of dimethylformamide. The solvent was drawn off from the combined filtrates with the help of a rotary evaporator. The product remained behind as a yellow, oily liquid and required no further purification.

Weight: 1033.7 grams corresponding to 95.6% of theory, light yellow liquid.

|  | $C_{16}H_{32}N_2O_5Si$ (360.525) | | |
|---|---|---|---|
| (SL30-3-1) | C | H | N |
| Calculated: | 53.30% | 8.94% | 7.77% |
| Found: | 53.66% | 9.36% | 7.33% |

Figure 1:
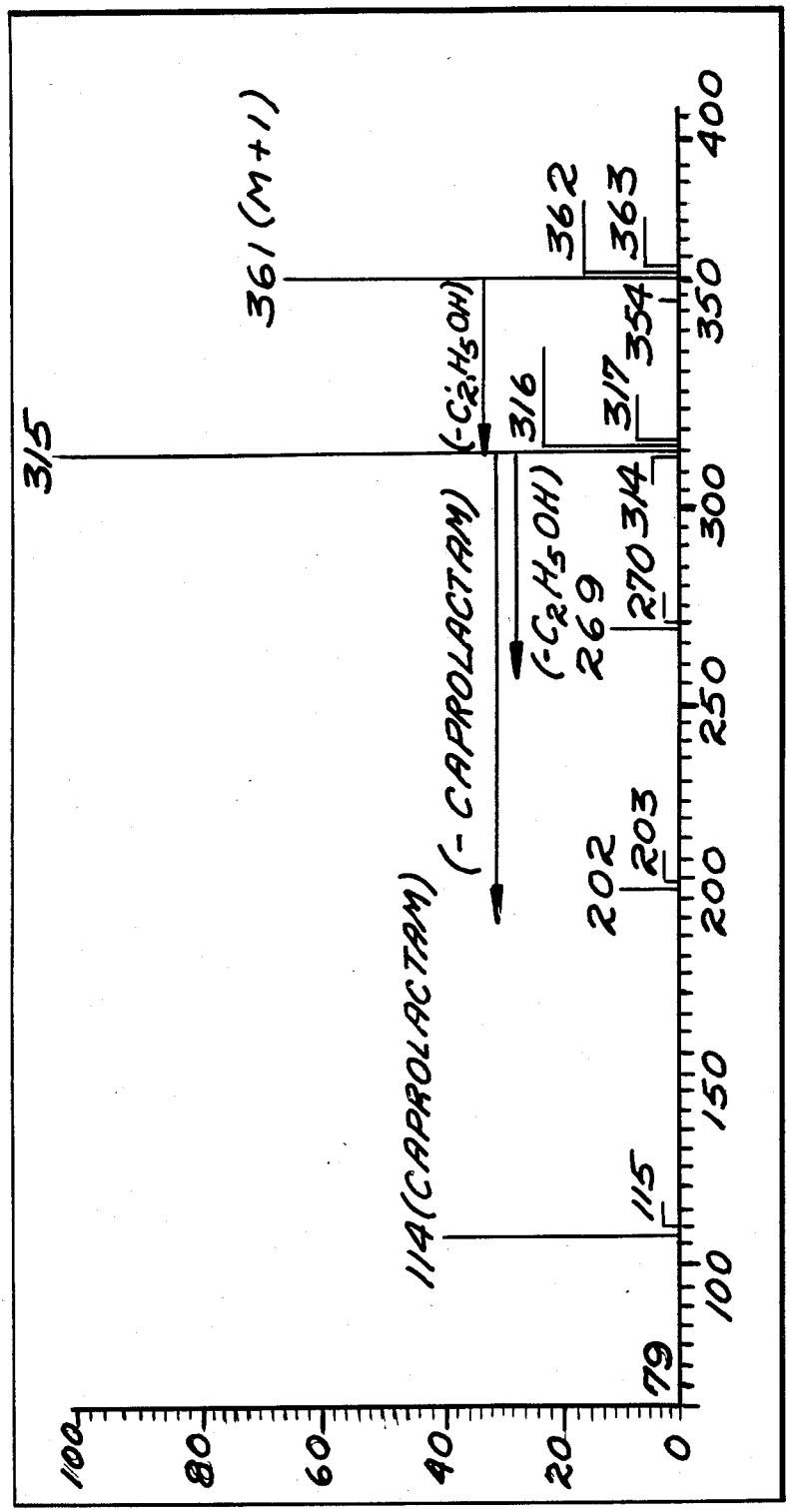
FIG. 1 is a mass spectrograph of the compound of Example 1.

The molecular weight was confirmed by means of mass spectrometry, see FIG. 1.

Figure 2:
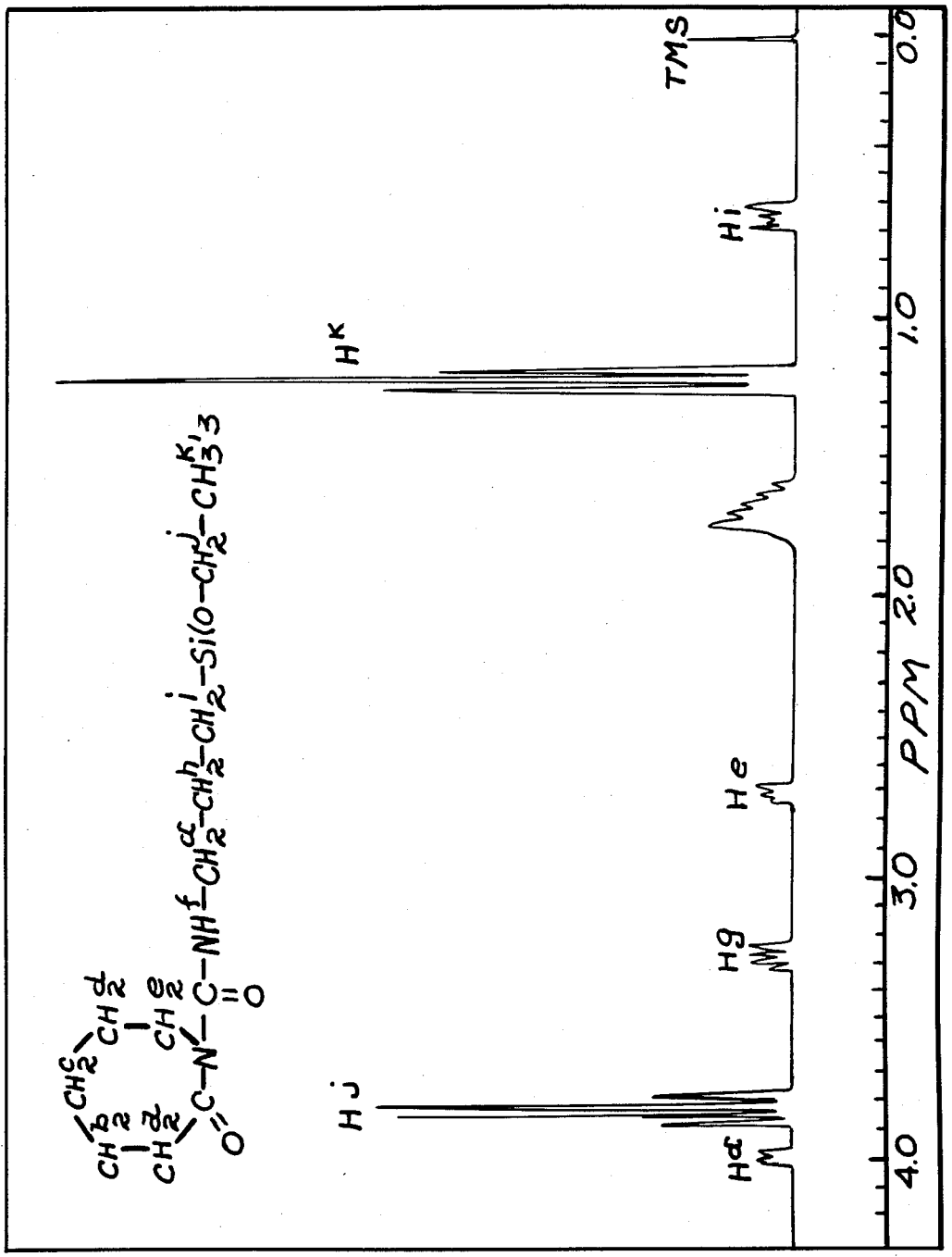
FIG. 2 is the ¹H-NMR spectrum of the compound of Example 1.
Figure 3:
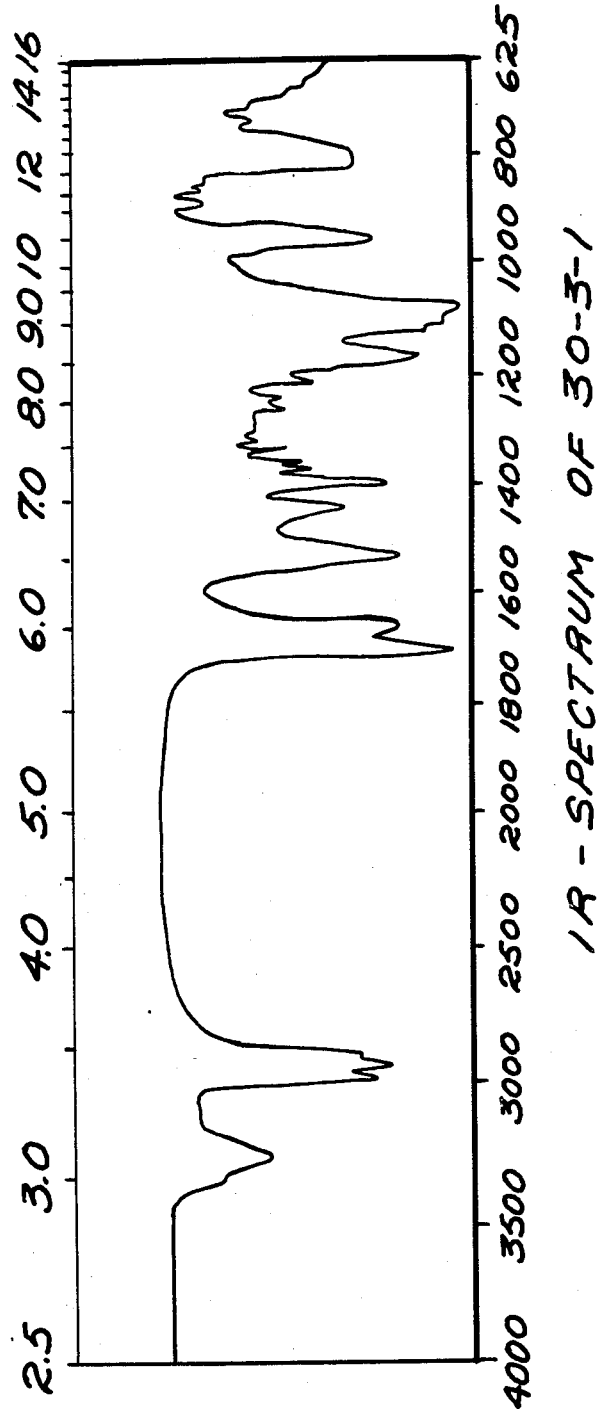
FIG. 3 is the IR spectrum of the compound of Example 1.

The $^1$H-NMR spectrum (250 MHz) as well as the IR spectrum of the product are shown as further characteristics of the product in FIGS. 2 and 3.

EXAMPLES 2 TO 8

As described in Example 1 there were produced 7 additional acylureas having hydrolyzable silyl groups by varying the starting material. The amount added and the type of material added are set forth in Table 1. Table 2 contains data for characterizing the product. All of the products were oily yellow to light brown liquids which did not have to be purified before use.

EXAMPLE 9

Thermolysis of an Acylurea and Distillative Separation of the Isocyanatopropylsilane 150 grams of the product obtained in Example 7 were heated in a vacuum distillation apparatus with a Vigreux column at a vacuum of 20 mbar≅2000 Pa. The thermal decomposition of the acylurea began at a sump temperature of 142° C. 90.2 grams of a colorless liquid passed over at a head temperature of 107°–116° C., which liquid was identified by $^1$H-NMR spectroscopy as a mixture of about 85% of 3-isocyanatopropyltrimethoxysilane and 15% ε-caprolactam. The reaction sump (58.7 grams) consists of ε-caprolactam and tris(trimethoxysilylpropyl)isocyanurate. By a following vacuum distillation at 1 mbar there were obtained from the distillate of the thermolysis 70.6 grams of 3-isocyanatopropyltrimethoxysilane, corresponding to a yield of 73% based on the amount of acylurea employed in the thermolysis.

EXAMPLE 10

Catalytic Splitting of an Acylurea 154.5 grams of the product obtained according to Example 7 were treated with 5 grams of dibutyltin dilaurate and heated in a vacuum distillation apparatus with a Vigruex column at a vacuum of 2 mbar≅200 Pa. The decomposition of the acylurea began at a sump temperature of 115° C. 100.3 grams of colorless liquid passed over at a head temperature of 77°–84° C., which liquid according to $^1$H-NMR spectroscopy represented a mixture of about 90% isocyanatopropyltrimethoxysilane and 10% ε-caprolactam. By a following vacuum distillation there were obtained therefrom 85.8 grams of 3-isocyanatopropyltrimethoxysilane, corresponding to a yield of 86% based on the amount of acylurea employed in the catalytic decomposition.

The entire disclosure of German priority application P 3524215.9 is hereby incorporated by reference.

TABLE 1

| | | | Starting Materials and Products | | | |
|---|---|---|---|---|---|---|
| Ex. | Amount Employed | Silane Employed | Acidamide | Alkali-cyanate | Solvent Amount | Product (Formula) |
| 2 | 0.5 mol | 3-chloropropyl-trimethylsilane | N—methyl-formamide | Potassium cyanate | DMF (150 ml) | $(CH_3O)_3Si-C_3H_6-NH-CO-N-CO-H$ <br> $\qquad\qquad\qquad\qquad\qquad\quad\|$ <br> $\qquad\qquad\qquad\qquad\qquad CH_3$ |
| 3 | 0.75 mol | 3-chloropropyl-trimethoxysilane | 2-pyrroli-done | Sodium cyanate | DMSO (250 ml) | $(CH_3O)_3Si-C_3H_6-NH-CO-N\underset{\diagdown}{\overset{\diagup CO\diagdown}{\qquad}}(CH_2)_3$ |
| 4 | 0.5 mol | 3-bromopropyl-triethoxysilane | 2-pyrroli-done | Potassium cyanate | DMF (200 ml) | $(C_2H_5O)_3Si-C_3H_6-NH-CO-N\underset{\diagdown}{\overset{\diagup CO\diagdown}{\qquad}}(CH_2)_3$ |

TABLE 1-continued

Starting Materials and Products

| Ex. | Amount Employed | Silane Employed | Acidamide | Alkali-cyanate | Solvent Amount | Product (Formula) |
|---|---|---|---|---|---|---|
| 5 | 0.5 mol | 3-iodopropyltri-n-propoxysilane | 2-pyrrolidone | Sodium cyanate | DMF (150 ml) | $(C_3H_7O)_3Si-C_3H_6-NH-CO-N\underset{(CH_2)_3}{\overset{CO}{\diagup\diagdown}}$ |
| 6 | 1 mol | 3-chloropropyl-trimethoxysilane | 2-piperidone | Potassium cyanate | N-Methyl pyrrolidone (300 ml) | $(CH_3O)_3Si-C_3H_6-NH-CO-N\underset{(CH_2)_4}{\overset{CO}{\diagup\diagdown}}$ |
| 7 | 1 mol | 3-chloropropyl-trimethoxysilane | ε-caprolactam | Potassium cyanate | DMF (300 ml) | $(CH_3O)_3Si-C_3H_6-NH-CO-N\underset{(CH_2)_5}{\overset{CO}{\diagup\diagdown}}$ |
| 8 | 0.2 mol | 3-chloropropyl-dimethoxymethylsilane | ε-caprolactam | Sodium cyanate | DMF (50 ml) | $(CH_3O)_2Si(CH_3)-C_3H_6-NH-CO-N\underset{(CH_2)_5}{\overset{CO}{\diagup\diagdown}}$ |

TABLE 2

Product Characterization

| Ex. | Product Amount | Yield | Summation Formula | Molecular Weight | Calculated: Found: | C | H | N |
|---|---|---|---|---|---|---|---|---|
| 2 | 115.4 g | 87.3% | $C_9H_{20}N_2O_5Si$ | 294,354 | | 40.89% | 7.63% | 10.60% |
|   |         |       |                    |         | | 40.93% | 7.76% | 11.18% |
| 3 | 209.7 g | 96.3% | $C_{11}H_{22}N_2O_5Si$ | 290.392 | | 45.50% | 7.64% | 9.65% |
|   |         |       |                    |         | | 45.27% | 8.17% | 9.88% |
| 4 | 162.4 g | 97.7% | $C_{14}H_{28}N_2O_5Si$ | 332,474 | | 50.58% | 8.49% | 8.43% |
|   |         |       |                    |         | | 50.17% | 9.03% | 8.39% |
| 5 | 182.8 g | 97.6% | $C_{17}H_{34}N_2O_5Si$ | 374,555 | | 54.52% | 9.15% | 7.48% |
|   |         |       |                    |         | | 54.56% | 9.55% | 7.54% |
| 6 | 298.9 g | 98.2% | $C_{12}H_{24}N_2O_5Si$ | 304,419 | | 47.35% | 7.95% | 9.20% |
|   |         |       |                    |         | | 47.68% | 8.23% | 9.45% |
| 7 | 304.5 g | 95.6% | $C_{13}H_{26}N_2O_5Si$ | 318,447 | | 49.03% | 8.23% | 8.80% |
|   |         |       |                    |         | | 48.54% | 8.66% | 8.43% |
| 8 | 55.9 g  | 92.5% | $C_{13}H_{26}N_2O_4Si$ | 302,448 | | 47.66% | 8.00% | 9.26% |
|   |         |       |                    |         | | 47.95% | 8.25% | 9.12% |

What is claimed is:

1. A N-silylpropyl-N'-acyl-urea of the formula:

$$A-\overset{O}{\underset{\|}{C}}-NH-C_3H_6-Si(CH_3)_x(OR)_{3-x} \quad (III)$$

in which
x is 0, 1, or 2
R is $C_1$–$C_6$ alkyl, (2'-methoxy)ethyl or aryl,
A is $$-\underset{\underset{R^1}{|}}{N}-\overset{O}{\underset{\|}{C}}-R^2$$

where $R^1$ is $C_1$–$C_6$ alkyl, $R^2$ is hydrogen, $C_1$–$C_6$ alkyl or
A is

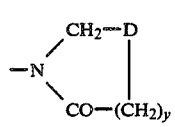

where y is 1, 2, or 3 and D is —$CH_2$—, or >$NR^1$.

2. A compound according to claim 1 where R is $C_1$–$C_6$ alkyl, (2'-methoxy)ethyl or phenyl.

3. A compound according to claim 2 where $R^2$ is hydrogen.

4. A compound according to claim 2 where $R^2$ is $C_1$–$C_6$ alkyl.

5. A compound according to claim 2 where A is:

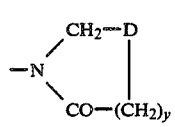

6. A compound according to claim 5 where D is —$CH_2$—.

7. A compound according to claim 6 where y is 3.

8. A compound according to claim 1 where x is 0.

9. A process for the production of a compound according to claim 1 comprising mixing in an aprotic, polar organic solvent equimolar amounts of an alkali cyanate, a 3-halopropyl silane of the formula:

$$X-C_3H_6-Si(CH_3)_x(OR)_{3-x} \quad (IV)$$

and a compound of the formula:

$$R^2-\overset{O}{\underset{\|}{C}}-NH-R^1 \text{ or} \quad (V)$$

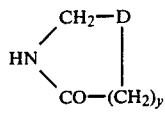

and X is Cl, Br or I, subsequently reacting them with each other at elevated temperature, after the end of the reaction cooling the reaction mixture to room temperature filtering off the precipitated alkali halide and distilling off the solvent from the filtrate.

10. A process according to claim 9 wherein the reaction is carried out at 100°–140° C.

11. A process according to claim 10 wherein there is employed ε-caprolactam.

12. A process according to claim 11 wherein the solvent is dimethylformamide.

13. A process according to claim 10 wherein the solvent is dimethylformamide.

14. A process for setting free the blocked isocyanate function from a compound according to claim 1 comprising thermolyzing the compound in a vacuum and distilling off the 3-isocyanatopropylsilane formed of the formula:

$$OCN-C_3H_6-Si(CH_3)_x(OR)_{3-x} \qquad (VII).$$

15. A process according to claim 14 including a second vacuum distillation.

16. A process according to claim 14 comprising carrying out the thermolysis in the presence of a catalytic amount of dibutyltin dilaurate.

* * * * *